United States Patent [19]

Weinland

[11] 4,105,540

[45] Aug. 8, 1978

[54] PHOSPHORUS CONTAINING COMPOUNDS AS ANTIFOULANTS IN ETHYLENE CRACKING FURNACES

[75] Inventor: Billy W. Weinland, Conroe, Tex.

[73] Assignee: Nalco Chemical Company, Oak Brook, Ill.

[21] Appl. No.: 860,793

[22] Filed: Dec. 15, 1977

[51] Int. Cl.² .................. C10G 9/16; C07C 11/04
[52] U.S. Cl. .................... 208/48 AA; 203/6; 208/348; 260/683 R
[58] Field of Search ............ 208/48 AA; 260/683 R

[56] References Cited

U.S. PATENT DOCUMENTS

| | | | |
|---|---|---|---|
| 2,899,387 | 8/1959 | Fierce et al. | 208/348 |
| 3,261,774 | 7/1966 | Newkirk et al. | 208/48 AA |
| 3,516,922 | 6/1970 | Anzilotti | 208/47 |
| 3,645,886 | 2/1972 | Gillespie et al. | 208/48 AA |
| 3,776,835 | 12/1973 | Dvoracek | 208/48 AA |
| 4,024,048 | 5/1977 | Shell et al. | 208/48 AA |
| 4,024,049 | 5/1977 | Shell et al. | 208/48 AA |
| 4,024,050 | 5/1977 | Shell et al. | 208/48 AA |
| 4,024,051 | 5/1977 | Shell et al. | 208/348 |

Primary Examiner—Delbert E. Gantz
Assistant Examiner—G. E. Schmitkons
Attorney, Agent, or Firm—John G. Premo; Robert A. Miller; Barry W. Sufrin

[57] ABSTRACT

Phosphate and phosphite mono and diesters in small amounts function as antifoulant additives in ethylene cracking furnaces which are subjected to elevated temperatures from about 500° – 1700° F. These furnaces produce material that deposits and accumulates upon furnace surfaces including furnace coils and transfer line exchangers. The present antifoulant additives inhibit and suppress fouling and also help clean up previously fouled furnace surfaces.

5 Claims, No Drawings

PHOSPHORUS CONTAINING COMPOUNDS AS ANTIFOULANTS IN ETHYLENE CRACKING FURNACES

BACKGROUND OF THE INVENTION

Ethylene manufacture entails the use of pyrolysis or "cracking" furnaces to manufacture ethylene from various gaseous and liquid petroleum feed stocks. Typical gaseous feed stocks include ethane, propane, butane and mixtures thereof. Typical liquid feed stocks include naphthas, kerosene, gas oil and crude oil.

Fouling of the cracking furnace coils and transfer line exchangers (TLEs) occurs due to coking and polymer deposition. The fouling problem probably is the major operational difficulty experienced in running an ethylene plant. Depending on deposition rate, ethylene furnaces must be periodically shut down for cleaning. In addition to periodic cleaning, "crash shut downs" are sometimes required due to dangerous increases in pressure or temperatures resulting from deposit build-up on furnace coils and TLEs. Cleaning operations are carried out either mechanically or by steam/air decoking.

Run lengths for ethylene furnaces average from one week to three months depending in part upon the rate of fouling of the furnace coils and TLEs. This fouling rate is in turn dependent upon the nature of the feed stock as well as upon furnace design and operating parameters. In general, however, heavier feed stocks and higher cracking severity result in an increased rate of furnace and TLE fouling.

In recent years, amine neutralized sulfonate treatments have been used in some ethylene plants to reduce furnace coil fouling. These compounds, however, have failed to prevent coking and fouling of TLEs immediately down stream of the furnace. The failure in respect of the TLEs may be due to premature degradation of the treatments in the ethylene furnace which sees temperatures in the range 1,000° – 1,700° F.

Applicants have now discovered that certain phosphate and phosphite mono and diesters will significantly reduce the fouling rate upon both the furnace coils and the transfer line exchangers. The use of these compounds as antifoulant additives in crude oil systems were previously described in U.S. Pat. Nos. 4,024,048, 4,024,049 and 4,024,050. The effectiveness of these compounds under the difficult conditions found in the ethylene cracking plant, however, has not been previously suggested.

BRIEF SUMMARY OF THE INVENTION

This invention entails an improved process for reducing the fouling tendencies experienced in ethylene cracking furnaces including the formation of coking and polymer deposition on furnace coils and transfer line exchangers. The treatment is effective over the temperature range 500° –1700° F. which are found in ethylene cracking furnaces.

The method involves treatment of feed stock with at least 10 ppm and, preferably 25 – 100 ppm of the phosphorus ester antifoulants described below. In addition, it is preferred that plant equipment surfaces be pretreated with these compounds in the absence of the feed stock. The phosphate ester compounds employed in this invention are characterized by the general formula:

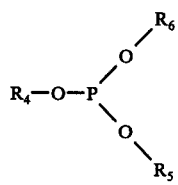

where $R_1$, $R_2$, and $R_3$ are each individually selected from the group consisting of hydrogen, addition complexes of hydrogen with amines, alkyl, aryl, alkaryl and cycloalklyl, alkenyl, and aralkyl, and provided that in any given such phosphate ester at least one and not more than two of each of $R_1$, $R_2$, and $R_3$ are hydrogen or an addition complex of hydrogen with an amine.

The phosphite ester compounds employed in this invention are characterized by the general formula:

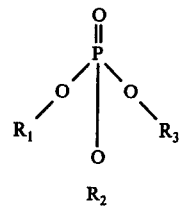

where: $R_4$, $R_5$, and $R_6$ are each individually selected from the group consisting of hydrogen, addition complexes of hydrogen with amines, alkyl, aryl, alkaryl and cycloalkyl, alkenyl, and provided that in any given such phosphite ester at least one and not more than two of each of $R_1$, $R_2$, and $R_3$ are hydrogen or an addition complex of hydrogen with an amine.

A compound of formulas (1) and (2) typically contains from about 1 to 50 carbon atoms per molecule and preferably from about 8 to 20. Presently preferred compounds of formulas (1) and (2) include those wherein $R_1$ and $R_2$ are each a same or different lower alkyl group, $R_3$ is an addition complex of hydrogen with an amine wherein the amine is a primary amine which contains at least one alkyl group per molecule, and each such amine alkyl group contains 8 through 14 carbon atoms each, $R_4$ is hydrogen, $R_5$ and $R_6$ are each a same or different alkyl group containing less than II carbon atoms each. The phosphate esters are preferred over the phosphite esters. As used herein, the term "lower" has reference to a group containing less than seven carbon atoms each.

The total number of carbon atoms for each of $R_1$, $R_2$ and $R_3$ can range between about 1 and 50, with a preferred range being from about 8 through 20 carbon atoms each. Typical examples of suitable phosphate esters include (the specific listing of a given monoester here is intended to include the like listing of the corresponding diester as well; thus, for example, methyl phosphate is intended to include dimethyl phosphate but, in instances where the $R_4$, $R_5$, and $R_6$ are not the same, the di-esters are specifically named): methyl phosphate, ethyl phosphate, n-propyl phosphate, isopropyl phosphate, butyl phosphate, pentyl phosphate, hexyl phosphate, cyclohexyl phosphate, heptyl phosphate, nonyl phosphate, decyl phosphate, lauryl phosphate, lorol phosphate, cetyl phosphate, octadecyl phosphate, heptadecyl phosphate, phenyl phosphate, alpha or beta naphthyl phosphate, alpha or beta naphthenyl phosphate, benzyl phosphate, tolyl phosphate, methyl phenyl phosphate, amyl phenyl phosphate, nonylphenyl phosphate, nonyl phenyl phosphate, 4-amylphenyl phosphate, isobutyl phenyl phosphate, nonyltolyl phosphate, di-polyisobutenyl phosphate, di-polyisobutenylphenyl phosphate, polyisobutenylphenyl phosphate, diphenyl phosphate; ethyl phosphate, di-polyisobutenyl, di-polyisobutenyl, and the like.

Many of these phosphate esters, particularly those containing the smaller number of carbon atoms per molecule, are readily available commercially. Methods of preparation of formula (1) compounds are conventional. Thus, for example, phosphorus pentoxide may be added to a solution of an alcohol in an organic solvent (aromatic solvents being slightly usually preferred over aliphatic solvents because of their more polar character). Examples of suitable solvents include kerosenes, heavy aromatic naphthas, and the like.

The resulting mixture is heated to an elevated temperature to produce reaction. The reaction products are typically soluble and remain in solution. Preferably, reactants are employed in stoichiometric amounts so that relatively pure product solutions are obtained, since the reactions tend to go to completion. Depending upon the particular alcohol reactant or reactants employed, the reaction temperatures used, as well as upon the respective quantities of reactants present, the reaction product is a phosphate ester having one or two alkyl or other hydrocarbonaceous substituents per molecule, as shown in formula (1) above.

A wide variety of alcohol reactants may be employed to realize specific compounds falling within the scope of formula (1). Phosphorus pentoxide is presently preferred as starting phosphorus compounds, but, as those skilled in the art will appreciate, a variety of other phosphorus compounds may be employed, such as phosphoric acid, phosphorus oxychloride, polyphosphoric acid, phosphorus anhydride, and the like.

The reaction product is usually and preferably one which contains at least one acidic hydrogen atom per molecule which is readily neutralized with a base, preferably for this invention a primary or a secondary amine.

Examples of suitable alcohols include normal, straight chain alcohols such as methanol, ethanol, and those wherein the hydrocarbon portion is n-propyl, n-butyl, n-amyl, n-hexyl, n-hepyl, n-octyl, n-nonyl, n-decyl, n-undecyl, n-dodecyl (lauryl), N-tetradecyl (myristyl), n-hexadecyl (cetyl), and n-octadecyl (stearyl); branched chain primary alcohols such as isobutyl, isoamyl, 2,2,4-trimethyl-1-hexanol and 5,7,7-trimethyl-2-(1,3,3-trimethylbutyl)-1-octanol; and secondary alcohols such as isopropyl, sec-butyl, 2-pentanol, 2-octanol, 4-methyl-2-pentanol, and 2,4-dimethyl-3-pentanol. Examples of alicyclic alcohols are cyclopentanol, cyclohexanol, cycleheptanol, and menthol. Examples of alcohols of the class having ethylenic unsaturation are allyl, crotyl, oleyl (cis-9-octadecen-1-ol), citronellol, and geraniol.

Acetylenic unsaturation is illustrated by propargyl alcohol. Araliphatic alcohols are illustrated by benzyl, 2-phenylethanol, hydrocinnamyl, and alpha-methylbenzyl alcohols. Cinnamyl alcohol is an example of an alcohol containing both aromatic and ethylenic unsaturation.

One excellent source of alcohol which may be used is that class of compounds known as oxo alcohols. These are normally a mixture of various intermediate molecular weight alcohols ranging from 4 to about 16 carbon atoms. Their preparation and description is described in the book *Higher Oxo Alcohols* by L. F. Hatch, Enjay Company, Inc., 1957, which disclosure is hereby incorporated by reference. The general range of both alcohols and ester by-products typifying an oxo alcohol still bottom of the type which may be used in the invention, is as follows:

| Ingredient | Percent |
| --- | --- |
| Mixed iso-and n-octyl alcohol | 2 – 20 |
| Mixed iso-and n-nonyl alcohol | 5 – 40 |
| Mixed iso-and n-decyl and higher alcohols | 25 – 90 |
| Esters | 20 – 80 |

Examples of suitable amines include n-Dodecyl amine; n-Tetradecyl amine; n-Hexadecylamine; lauryl amine, myristyl amine; palmityl amine; stearyl amine; oleyl amine; coconut oil amine; tallow amine; hydrogenated tallow amine; cottonseed oil amine; dilauryl amine; dimyristyl amine; dipalmityl amine; distearyl amine; dicoconut amine; dihydrogenated tallow amine; octyl methylamine; octadecyl methyl amine; hexylethyl amine; soya amine 10%; octadecyl 10%, octadaemyl 35%; octadecadienyl 45%; ethyl amine; diethyl amine; morpholine; butyl amine; isopropylamine; diisopropylamine; N-methyl morpholine; triethylamine; aminoethyl ethanolamine; diethanolamine; diethyl ethanolamine; diisopropanol amine; diemethyl-ethanolamine; dimethyl isopropanolamine; N-hydroxy ethyl morpholine; N-methyldiethanolamine; monoethanolamine; monoisopropanolamine; triethanolamine; triisopropanolamine; 1,1-dihydroxymethyl ethylamine; 1,1-dihydroxymethyl-n-propylamine; polyglycolamine $(H_2NCH_2CH_2-O-CH_2CH_2)_nOH$ where $n = 1$ to 10 inclusive; pyrrolidone; 5-methyl-2-oxazolidone; 2-oxazolidone; imidazole; polyamines of the class

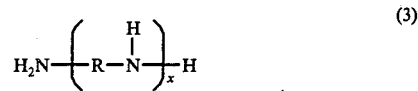
(3)

where R is an alkylene radical selected from among

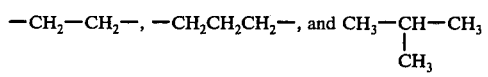

and $x$ is an integer of 1-5; 5-benzimidazole; 2-hydroxyethyl imidazole; 2-methyl imidazole; pyrazine; pyridine; piperidine, 2-cyanomethyl-2-imidazoline; cyclohexyl amine, and the like.

One preferred class of amines are highly substituted imidazolines such as those defined by one of the following formulas:

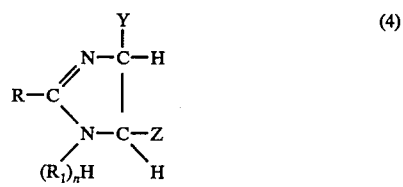
(4)

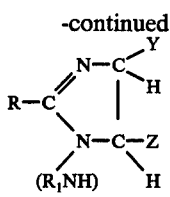 (5)

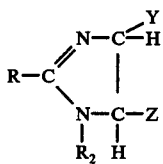 (6)

where in formulas (4), (5), and (6) above R is an aliphatic group of from about 1 to 22 carbon atoms in chain length, Y and Z are selected from the group consisting of hydrogen and lower aliphatic hydrocarbon groups of not more than 6 carbon atoms in chain length, $R_1$ is an alkylene radical of about 1 to 6 carbon atoms, $R_2$ is a radical selected from the group consisting of R and hydrogen, and $n$ is an integer of from about 1 to 50. Imidazolines of the type shown in Formulas (4), (5) and (6) are conveniently prepared by reacting a monocarboxylic acid such as a saturated or unsaturated fatty acid with an alkylene polyamine or hydroxyalkyl alkylene diamine in accordance with well-known methods. The product imidazolines may be further reacted via oxyalkylation to produce other useful derivatives. Methods of preparing imidazolines of this type are given in the article, "The Chemistry of the s-Imidazolines and Imidazolidines", by R. J. Ferm and J. L. Riebsomer, Chemical Reviews, Vol. 54, No. 4, August, 1954. Particularly useful imidazolines for use in the practice of the invention are those described in Wilson U.S. Pat. Nos. 2,267,965 and 2,355,837. Two typical imidazolines of the type described by the formulas above are 1-(2 hydroxyethyl)-coco imidazoline and 1-(2 hydroxyethyl)-2 tall oil imidazoline, both of which compounds are conveniently prepared using the teachings of Wilson U.S. Pat. No. 2,267,965.

For purposes of illustrating several other types of typical imidazolines that may be used, the following are given by way of example:

1-(2-hydroxyethyl)-2-undecyl imidazoline
1-(2-hydroxyethyl)-2-tridecyl imidazoline
1-(2-hydroxyethyl)-2-pentadecyl imidazoline
1-(2-hydroxyethyl)-2-heptadecyl imidazoline
1-(2-aminoethyl)-2-heptadecyl imidazoline
1-(2-aminoethyl)-aminoethyl-1-2-undecyl imidazoline
1-(2-aminoethyl)-aminoethyl-1-2-tridecyl imidazoline The fatty acids are most generally reacted with a polyalkylene polyamine such as diethylene triamine, triethylene tetramine, tetraethylene pentamine, or mixtures thereof, or a polyamine alcohol such as aminoethyl ethanolamine. The amine may likewise be substituted with lower alkyl groups.

A particularly preferred class of amines are tertiary-alkyl primary amines. The tertiary-alkyl primary amines have the formula:

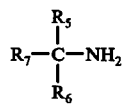 (7)

More specifically, the tertiary-alkyl primary amine constitutes a component wherein $R_5$ and $R_6$ are lower alkyl groups, usually methyl groups, and $R_7$ constitutes a long chain alkyl radical composed of 8 to 19 carbons. Tertiary-alkyl primary amines which have been found eminently suitable for the instant invention are "Primene 81-R" and "Primene JM-T". "Primene 81-R" is reported by its manufacturer to be composed of principally tertiary-alkyl primary amines having 11-14 carbons and has a molecular weight principally in the range of 171-213, a specific gravity of 25° C of 0.813, a refractive index of 1.423 at 25° C and a neutralization equivalent of 191. "Primene JM-T" is reported by the manufacturer to be composed of tertiary-alkyl primary amines having 18-22 carbons with a molecular weight principally in the range of 269-325, a specific gravity at 25° C of 1,456 and a neutralization equivalent of 315.

The primary constituent of "Primene 81-R" is reported to be:

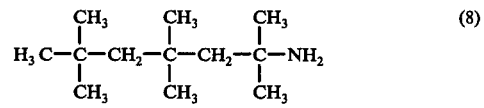 (8)

The primary constituent of "Primene JM-T" is reported to be essentially the same structure as "Primene 81-R", but with 22 carbons. "Primene" is a trademark of the Rohm & Haas Company for its brand of tertiary alkyl primary amines.

Phosphite Compounds

The total number of carbon atoms for each $R_4$, $R_5$ and $R_6$ can range between about 1 and about 50 with the preferred range being between about 8 and 20 carbon atoms per hydrocarbon radical. Typical examples of suitable phosphite esters include (the specific listing of a given monoester here is intended to include the like listing of the corresponding diester as well; thus, for example, methyl phosphite is intended to include dimethyl phosphite, but in instances where the $R_4$, $R_5$ and $R_6$ are not the same, the diesters are specifically named): methyl phosphite, ethyl phosphite, n-propyl phosphite, isopropyl phosphite, butyl phosphite, pentyl phosphite, hexyl phosphite, cyclohexyl phosphite, heptyl phosphite, nonyl phosphite, decyl phosphite, lauryl phosphite, lorol phosphite, cetyl phosphite, octadecyl phosphite, heptadecyl phosphite, phenyl phosphite, alpha or beta naphthyl phosphite, alpha or beta naphthenyl phosphite, benzyl phosphite, tolyl phosphite, methyl phenyl phosphite, amyl, phenyl phosphite, diamyl phenyl phosphite, nonylphenyl phosphite, isobutyl phenyl phosphite, nonyltolyl phosphite, di-polyisobutenyl phosphite, di-polyisobutenylphenyl phosphite, polyisobutenylphenyl phosphite, diphenyl phosphite, di-polyisobutenyl, di-polyisobutenyl, and the like.

Many of these phosphite esters, particularly those containing a small number of carbon atoms per molecule, are readily available commercially. Methods of preparation are conventional. Some of these esters, particularly those having the longer alkyl chains although presently not available commercially, are readily prepared by reacting one, two, or three moles of the corresponding alcohol or phenol with each mole of a phosphorus trihalide, such as phosphorus trichloride or phosphorus tribromide. This is a conventional reaction and there are other ways, also conventional, of producing these various phosphite esters. Thus, organophosphites may be conveniently prepared by direct esterization of phosphorous acid with alcohol.

The present invention is not concerned with the particular method by which the phosphite esters or phosphate esters are produced. In those cases where mono- or di-esters are formed, it is sometimes desirable, following the esterification reaction, to treat the reacted mixture with water, dilute aqueous caustic, or dilute aqueous mineral acid in order to hydrolyze off the residual chlorine of bromine atoms present by reason of the particular trivalent or pentavalent phosphorus compound employed as an original reactant. Amine salts of phosphite esters do not appear to be as active antifoulants as do other materials of formulas (1) and (2).

EXAMPLES

Commercial ethylene plants were treated with the organophosphorous antifoulants with results are reported below.

1. A commercial plant employing selas furnaces and using ethane and propane refinery gasses was treated, based on furnace feed rates, with 75 ppm by weight of a treatment composition comprising:
18.0% Kerosene
29.1% Isooctanol
10.7% Phosphorus Pentoxide
42.2% Primene 81-R To this product solution is added with stirring 246 grams of "Primene 81-R." "Primene 81-R" is a trademark of the Rohm & Haas Company for its brand of principally tertiary-alkyl primary amines having 11 - 14 carbons which have a molecular weight principally in the range of 171 - 213, a specific gravity at 25° C. of 0.813, a refractive index of 1,423 at 25° C. and a neutralization equivalent of 191. The resulting product is a 50 weight percent solution of amine salt of mixed octyl phosphates in mixed xylenes. Reaction conditions to produce the resulting octyl phosphates is described in Example 1 of U.S. Pat. No. 4,024,048.

The treatment composition was diluted 4:1 with gas oil and injected into the hydrocarbon feed line ahead of the feed line header which feeds the plants furnaces. Run lengths of 50 - 60 days up to 121 days were achieved with a reduction in the number of "crash shutdowns" required.

2. Another ethylene plant using ethane refinery gas and 25 ppm by weight of the Example 1 treatment composition based on furnace hydrocarbon rates was studied. Application of the treatment composition diluted 4:1 was injected into each coil of the furnace. The low dosages were made possible by the direct injection approach which avoids distribution problems associated with injection into the furnace header.

Untreated furnaces in the plant under study when operated on straight ethane generally ran 300 - 350 hours before reaching unacceptable pressure drops across the TLEs. The first test using the Example 1 composition produced a run length of 390 hours. More significantly, however, was the fact that the deposit formation on the TLE tube sheet and inside the tubes was much less severe than normal.

A second run with the treatment composition went for 1324 hours. The TLE tube sheet appeared to be much cleaner than expected after such a long run. Unfortunately, the supply of the treatment composition ran out at about the 1000 hour mark and so the pressure drop accelerated during this period.

Two further runs were made with the treatment composition. The first run was made at dosages below 25 ppm and resulted in a run of 650 hours.

3. Foster-Wheeler vertical furnaces with 6 inch tubes using ethane-propane refinery gasses were treated with an amine-neutralized sulfonate. Dosages were made at 20 - 25 ppm based on the hydrocarbon feed rate to the furnace. The treatment composition of Example 1 at 75 ppm based on the hydrocarbon charge was then applied to the TLEs. The Example 1 treatment composition was dispersed into water and injected through four quench jets between the furnace outlet and the TLE.

This test was designed to overcome the TLE coking-/fouling problems which remained in spite of the sulfonate treatment.

Plant operators had not permitted the plant to run longer than 45 days in the past due to fouling of the TLE. Use of the Example 1 treatment composition made possible a run of 80 days.

Having thus described my invention, it is claimed as follows:

1. A method for reducing fouling in ethylene cracking furnaces using petroleum feedstocks comprising treating the petroleum feedstocks with at least 10 ppm of a compound chosen from the group consisting of phosphite and phosphate esters, said phosphate esters being characterized by the general formula:

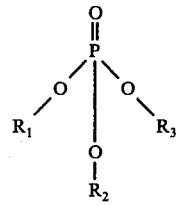

where: $R_1$, $R_2$, and $R_3$ are each independently selected from the group consisting of hydrogen, an addition complex of hydrogen with an amine, alkyl, aryl, alkaryl, cycloalkyl, alkenyl, and aralkyl, provided that in any given such phosphate ester at least one and not more than two of each of $R_1$, $R_2$, and $R_3$ are each hydrogen or an addition complex of hydrogen with an amine, and said phosphite esters characterized by the general formula:

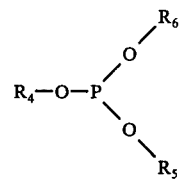

where: $R_4$, $R_5$ and $R_6$ are each independently selected from the group consisting of hydrogen, an addition complex of hydrogen and an amine, alkyl, aryl, alkaryl, cycloalkyl, alkenyl, and aralkyl, provided that in any given such phosphite ester at least one and not more than two of each of $R_4$, $R_5$, and $R_6$ are each hydrogen or an addition complex of hydrogen with an amine.

2. The method of claim 1 wherein said additive is first dissolved in a heavy aromatic hydrocarbon having a boiling point in the range from about 350° - 550° C. before being admixed with said petroleum feed stocks.

3. The method of claim 1 wherein, in each such phosphate compound, $R_1$ and $R_2$ are each lower alkyl and $R_3$ is a hydrogen addition complex with an amine.

4. The method of claim 1 wherein, in each such phosphite compound, $R_4$ and $R_5$ are each lower alkyl and $R_6$ is hydrogen.

5. The method of claim 1 wherein said phosphate compound is either mixed octyl phosphate amine salt or a mixed butyl phosphate amine salt.

* * * * *